(12) United States Patent
Loelsberg et al.

(10) Patent No.: US 10,544,049 B2
(45) Date of Patent: Jan. 28, 2020

(54) PROCESS FOR PREPARING A POROUS INORGANIC POWDER

(71) Applicant: BASF SE, Ludwigshafen (DE)

(72) Inventors: Wibke Loelsberg, Osnabrueck (DE); Marc Fricke, Osnabrueck (DE); Mark Elbing, Bremen (DE); Dirk Weinrich, Osnabrueck (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/528,308

(22) PCT Filed: Nov. 16, 2015

(86) PCT No.: PCT/EP2015/076659
§ 371 (c)(1),
(2) Date: May 19, 2017

(87) PCT Pub. No.: WO2016/079040
PCT Pub. Date: May 26, 2016

(65) Prior Publication Data
US 2017/0341945 A1    Nov. 30, 2017

(30) Foreign Application Priority Data

Nov. 20, 2014  (EP) .................................. 14194007

(51) Int. Cl.
| | |
|---|---|
| *A61K 8/02* | (2006.01) |
| *A61K 8/25* | (2006.01) |
| *E04B 1/74* | (2006.01) |
| *A61Q 19/00* | (2006.01) |
| *B01J 13/00* | (2006.01) |
| *C01B 33/158* | (2006.01) |

(52) U.S. Cl.
CPC .......... *C01B 33/158* (2013.01); *A61K 8/0279* (2013.01); *A61K 8/25* (2013.01); *A61Q 19/00* (2013.01); *B01J 13/0091* (2013.01)

(58) Field of Classification Search
CPC .. C01B 33/158; B01J 13/0091; A61K 8/0279; A61K 8/25; A61Q 19/00
See application file for complete search history.

(56) References Cited

U.S. PATENT DOCUMENTS

| | | |
|---|---|---|
| 5,122,291 A | 6/1992 | Wolff et al. |
| 6,764,667 B1 | 7/2004 | Steiner, III |
| 2003/0109421 A1 | 6/2003 | Palakodaty et al. |
| 2005/0107252 A1 | 5/2005 | Gaffney et al. |
| 2005/0192366 A1 | 9/2005 | Ou et al. |
| 2008/0152715 A1 | 6/2008 | Shin et al. |
| 2009/0258132 A1 | 10/2009 | Westhoff et al. |
| 2010/0119432 A1* | 5/2010 | Yeo ..................... C01B 33/1585 423/338 |

FOREIGN PATENT DOCUMENTS

| | | |
|---|---|---|
| EP | 1 199 280 A1 | 4/2002 |
| EP | 1 531 001 A1 | 5/2005 |
| GB | 2 322 326 A | 8/1998 |
| WO | WO 00/24799 A1 | 5/2000 |
| WO | WO 02/32462 A1 | 4/2002 |
| WO | WO 2012/041823 A1 | 4/2012 |

OTHER PUBLICATIONS

International Search Report and Written Opinion of the International Searching Authority dated Jan. 18, 2016 in PCT/EP2015/076659 filed Nov. 16, 2015.
International Preliminary Report on Patentability dated Feb. 6, 2017 in PCT/EP2015/076659 filed Nov. 16, 2015.
A. Hertz, et al., "Robust Synthesis of Yttria Stabilized Tetragonal Zirconia Powders (3Y-TZPs) Using a Semi-Continuous Process in Supercritical $CO_2$," Chemical Engineering Journal, vol. 228, 2013, pp. 622-630.
A. Montes, et al., "Silica Microparticles Precipitation by Two Processes Using Supercritical Fluids" The Journal of Supercritical Fluids, vol. 75, 2013, pp. 88-93.

* cited by examiner

*Primary Examiner* — Melvin C. Mayes
*Assistant Examiner* — Michael Forrest
(74) *Attorney, Agent, or Firm* — Oblon, McClelland, Maier & Neustadt, L.L.P.

(57) ABSTRACT

The present invention is directed to a process for preparing an inorganic aerogel, the process comprising the steps of providing a composition (I) suitable to form an inorganic gel with a gelation time $t_G$, spraying the composition (I) into supercritical carbon dioxide at a spraying time $t_S$ to obtain gel particles, and drying the gel particles obtained in step (ii) by supercritical liquid extraction, wherein the ratio $t_S:t_G$ is in the range of from 0.2 to 0.99. The present invention further is directed to the inorganic aerogel as such as well as the use of the inorganic aerogel according to the invention in particular for medical and pharmaceutical applications or for thermal insulation.

9 Claims, No Drawings

PROCESS FOR PREPARING A POROUS INORGANIC POWDER

The present invention is directed to a process for preparing an inorganic aerogel, the process comprising the steps of providing a composition (I) suitable to form an inorganic gel with a gelation time $t_G$, spraying the composition (I) into supercritical carbon dioxide at a spraying time $t_S$ to obtain gel particles, and drying the gel particles obtained in step (ii) by supercritical liquid extraction, wherein the ratio $t_S:t_G$ is in the range from 0.2 to 0.99, herein also referred to as relative spray time. The present invention further is directed to the inorganic aerogel as such as well as the use of the inorganic aerogel according to the invention in particular for medical, biomedical and pharmaceutical applications or for thermal insulation.

Porous materials such as inorganic aerogels are suitable for various applications. Porous materials having pores in the size range of a few microns or significantly below and a high porosity of at least 70% are for example particularly good thermal insulators on the basis of theoretical considerations.

Organic and inorganic aerogels and xerogels as well as processes for their preparation are known from the state of the art. Such porous materials having a small average pore diameter can be, for example, in the form of aerogels or xerogels which are produced with a sol-gel process and subsequent drying. In the sol-gel process, a sol based on a reactive gel precursor is first produced and the sol is then gelled by means of a crosslinking reaction to form a gel. To obtain a porous material, for example an aerogel, from the gel, the liquid has to be removed. This step will hereinafter be referred to as drying in the interests of simplicity.

The sol-gel method using metal oxides or metal alkoxides as starter compounds typically involves batch hydrolysis of precursor materials and condensation reactions where polymerization and gelling occurs. In certain instances a batch procedure has limitations. As an alternative, processes are available which use a particle precipitation.

EP1199280 discloses a process for the preparation of metal chalcogenides from solution or suspension via atomizing into a $CO_2$ containing autoclave with pressures from 1-50 MPa and a protic solvent. $CO_2$ here acts as an acid in the protic solvents required for generating the final products via reduction, oxidation or disproportionation. The precipitate, which is formed on the surface of inert support material particles, is then recovered by stepwise extracting the solvent with supercritical $CO_2$.

US20080152715 discloses the preparation of nano-particulate therapeutic agents by spraying a solution of vitamin K and a biodegradable polymer into a reactor containing supercritical $CO_2$. The bipolar polymer is essential as a surfactant to prevent flocculation of the particles, which are precipitated by rapidly blending the solvent and supercritical $CO_2$. Complete stepwise extraction of solvent is necessary to prevent the particles from re-dissolving in residual solvent, prior to collecting the powder-like product.

WO2002032462 discloses a process for preparing very fine particles of an active substance and a cyclodextrine as a host molecule being dissolved in an organic solvent. The solutions are brought in contact with supercritical $CO_2$ right before entering the atomizing chamber via an orifice to induce precipitation by anti-solvent effect. After purging the chamber with fresh $CO_2$ and depressurizing the particles can be recovered from the filter bed.

GB2322326 discloses a process for preparing fine particles of nicotinic acid using solution enhanced dispersal by supercritical fluids (SEDS) in a dual jet mode with two opposing inlet nozzles. One nozzle sprays a stream of supercritical $CO_2$ and a stream of nicotinic acid in ethanol in parallel to each other while a second nozzle sprays supercritical $CO_2$ in direction of the first nozzle. The nozzle diameter determines the particle size. Here, supercritical $CO_2$ is used to extract the substance from the solvent and to prepare particulate a material thereof.

US2003109421 discloses a process for preparing particles of temperature sensitive substances by a solvent anti-solvent extraction process. A solution or suspension of the target substance enters the particle formation vessel through a first location and a supercritical anti-solvent enters the same vessel through a second location further downstream at a distinctive angle allowing the anti-solvent to extract the solvent in order to promote particle formation. The particle formation vessel is kept under a temperature and pressure above the critical values of the anti-solvent.

US2009258132 discloses a process for the preparation of edible, heat-sensitive particles by spraying a mixture of an aqueous emulsion of fat, carbohydrates or polypeptides and a super-critical carrier medium such as $CO_2$ into a precipitating unit. Thereby the material is extracted from the aqueous medium whilst encapsulating a certain amount of $CO_2$ to induce the formation of spherical foam-building particles. Particle separation is carried out by a filter or cyclone after depressurizing.

Chem. Eng. J. 2013, 228, 622 discloses a semi-continuous precipitation with compressed anti-solvent (PCA) process for the preparation of yttria-stabilized zirconia nano-particles starting form a sol-gel reaction. In the process described the two starting materials are dissolved in iso-propanol, the condensation reaction is initiated by addition of nitric acid and the reaction mixture into the reaction vessel, which is preloaded with supercritical $CO_2$ (350° C., 23 MPa). The particle size is influenced by the rate of mechanical stirring of the reacting material in the vessel. At the end of the procedure the reaction vessel is depressurized.

J. of supercritical Fluids 2013, 75, 88-93 discloses the semi-continuous precipitation of silica microparticles via supercritical anti-solvent (SAS) process. Prior to particle formation, a gel is preformed from TEOS and an acidified water/ethanol mixture, which was aged for 3, 8 and 21 days at 277 K in air under atmospheric pressure. Precipitation was achieved by spraying the mixture into a flowing stream of supercritical $CO_2$ (313 K, 120 bar), which acts as an anti-solvent and removes organic solvent from the particles. After 2 h of washing with fresh supercritical $CO_2$, the pressure is released and the particles are removed. Particle size was found to depend on the degree of supersaturation as well as the solute concentration.

The processes as disclosed in the state of the art either describe particle formation of unreactive material or describe chemical reactions in a $CO_2$ filled autoclave with $CO_2$ acting as a reagent (EP1199280) or depict the preparation of nano-scaled zirconia particles in $CO_2$ at suitably high pressure and temperature for reaction In all cases the resulting powders are not sufficiently porous.

It was therefore an object of the invention to provide a process for the preparation of an inorganic aerogel with small particle size and high porosity, directly merging the chemical gel formation step with the subsequent drying step into one setup in order to obtain porous particles.

According to the present invention, this object is achieved by a process for preparing an inorganic aerogel, the process comprising the steps (i) providing a composition (I) suitable to form an inorganic gel with a gelation time $t_G$, (ii) spraying the composition (I) into supercritical carbon dioxide at a spraying time $t_S$ to obtain gel particles, (iii) drying the gel particles obtained in step (ii) by supercritical liquid extraction, wherein the ratio $t_S:t_G$ is in the range of from 0.2 to 0.99.

It has been surprisingly found that particle characteristics such as size distribution, porosity of the final aerogel and its pore size distribution can be addressed to a major extent by the choice of relative spray time. This allows for the production of tailor made aerogel particles.

It is important to spray the composition (I) at a given time with a given viscosity. In general the system needs to be sprayed before the gelpoint is reached, meaning the system needs to have a certain degree of flow ability. When preforming oscillatory rheometric measurements at such compositions (I) the loss factor G" is bigger than the storage modulus G' as long as the system is abled to flow=G">G'. When the system can't flow anymore the reversed case is true: the storage modulus G' is bigger than G"=G'>G". Therefore the gelation point can be given as the point as the cross over point, where G' becomes equal to G" or bigger as G"=G'≥G".

The process according to the present invention comprises steps (i) to (iii). According to step (i), a composition (I) suitable to form an inorganic gel with a gelation time $t_G$ is provided. This composition (I) is sprayed into supercritical carbon dioxide at a spraying time $t_S$ to obtain gel particles according to step (ii). The gel particles obtained in step (ii) are dried by supercritical liquid extraction. In the context of the present invention, the gelation time $t_G$ is defined as the time from initiating the gel formation until a gel has been formed which is indicated by a strong viscosity increase. In case the gel is formed by acid hydrolysis of the inorganic precursor and subsequent base induced gel formation, the gel formation is initiated by mixing the components which form the gel. The gelation time $t_G$ thus is the time from mixing the components which form the gel until a gel has been formed. The spraying time $t_S$ is defined as the time from mixing the components until composition (I) is sprayed into supercritical carbon dioxide. According to the present invention, the ratio $t_S:t_G$ is in the range of 0.2 to 0.99. The spraying time $t_S$ is chosen to be smaller than the gelation time $t_G$ according to the present invention, i.e. before the gelation is finished. The reacting sol is injected into the autoclave with a flow rate in the range from 10-999 ml/min. Where the flow rate is the speed of sol addition into the autoclave given as volume injected in a given time.

According to one specific embodiment, the present invention is directed to a process for preparing aerogel particles, in particular silica based aerogel particles, by spraying a reacting sol into an autoclave, which is filled with $CO_2$ in its supercritical state.

In the context of the present invention, composition (I) is suitable for forming an inorganic gel with a gelation time $t_G$. According to the present invention, an inorganic gel can also comprise organic components. The gelation time is adjusted to allow the steps of the process to be carried out. Any composition might be used in the context of the present invention as composition (I) as long as it is suitable for forming an inorganic gel. A suitable precursor might be used. In principle, a gel can be prepared by hydrolysis of a suitable precursor and subsequent condensation (gelation). Therefore, preferably composition (I) comprises a suitable precursor in a suitable solvent or mixture of solvents, water, a catalyst or a mixture thereof, and optionally a hydrophobizing agent as well as an opacifier.

The extent of hydrolysis may be controlled so that on average, each monomer is hydrolyzed to a desired level up to fully hydrolyzed on average. Each hydrolyzed monomer can undergo a condensation reaction with another monomer to form linked monomers, which are also referred to as polymers. A hydrolyzed monomer may also react with a polymer to form a larger polymer. A polymer is made up of two or more linked monomers. Linkage of a small number of monomers may be referred to as oligomers. Linkage of larger numbers of monomers may be referred to as resulting in polymers. While all oligomers are polymers, not all polymers are oligomers. Linkage formation may be enhanced by the use of a catalyst for the hydrolysis/condensation reactions, increase of water and, or precursor concentration and variation of reaction temperature.

Suitable precursor concentrations are for example in the range from 15 to 90 wt %, preferably 20 to 80 wt %, more preferably in the range from 25 to 70 wt %. Suitable concentrations of the hydrophobizing agent are for example in the range from 0.5 to 55 wt %, preferably 0.7 to 50 wt %, more preferably in the range from 1 to 45 wt %. Water can be present in an amount of from 2 to 45 wt %, preferably 3.5 to 35 wt %, more preferably from 5 to 25 wt %. A catalyst can be used in an amount of from 0.04 to 5 wt %, preferably 0.07 to 4 wt %, in particular 0.1 to 3 wt %. In case a combination of acid and base is used, the sum of the amount of acid and the amount of base generally is in the range from 0.04 to 5 wt %, preferably 0.07 to 4 wt %, in particular 0.1 to 3 wt %.

The gel material precursors for embodiments of the present invention may be inorganic, or a mixture of organic and inorganic components. Sols can be catalyzed to induce gelation by several methods. Examples include adjusting the pH and/or temperature of a dilute metal oxide sol to a point where gelation occurs. Suitable materials for forming inorganic aerogels are oxides of metals, transition metals and semimetals that can form oxides, such as silicon, aluminum, titanium, zirconium, hafnium, yttrium, vanadium, and the like.

The principal synthetic route for the formation of an inorganic aerogel may be the hydrolysis and condensation of an appropriate metal alkoxide.

Suitable precursors for the gelation are known to the person skilled in the art. The invention is not limited by the nature or type of the precursor(s) used. The precursor(s) may be inorganic, organic or a combination of inorganic/organic hybrid materials. Non-limiting examples of inorganic materials include alkoxides, aryloxides and acetylates of metals, non-metals and semi-metals, silanes, siloxanes, magnesium, calcium, strontium, scandium, yttrium, lanthanum, cerium, praesodym, neodymium, samarium, europium, erbium, ytterbium, lutetium, titanium, zirconium, hafnium, vanadium, niobium, tantalum, chromium, molybdenum, tungsten, rhenium, iron, cobalt, nickel, copper, zinc, cadmium, mercury, boron, aluminum, indium, silicon, germanium, tin, lead, bismuth, magnesium oxide, calcium oxide, magnesium fluoride, or calcium fluoride, or any combination of two or more of the above. Precursor may further include derivatives of any of the following or an equivalent thereof. For example, oxides of magnesium, calcium, strontium, scandium, yttrium, lanthanum, cerium, praesodym, neodymium, samarium, europium, erbium, ytterbium, lutetium, titanium, zirconium, hafnium, vanadium, niobium, tantalum, chromium, molybdenum, tungsten, rhenium, iron, cobalt, nickel, copper, zinc, cadmium, mercury, boron, aluminum, indium, silicon, germanium, tin, lead and bismuth made from metal alkoxides including but not limited to $Mg(OR)_2$, $Ca(OR)_2$, $Sr(OR)_2$, $Sr(OR)_3$, $Sc(OR)_3$, $Y(OR)_3$, $La(Or)_3$, $Ce(OR)_4$, $Pr(Or)_3$, $Nd(Or)_3$, $Sm(OR)_3$, $Eu(OR)_2$, $Eu(OR)_3$, $Er(OR)_3$, $Yb(OR)_3$, $Lu(Or)_3$, $Ti(OR)_4$, $Zr(OR)_4$, $Hf(OR)_4$, $V(OR)_3$, $Nb(OR)_4$, $Nb(OR)_5$, $Ta(OR)_4$, $Ta(OR)_5$, $Cr(OR)_3$, $Cr(OR)_4$, $Mo(OR)_4$, $W(OR)_4$, $W(OR)_5$, $W(OR)_6$, $Mn(OR)_2$, $Re(OR)_5$, $Fe(OR)_2$, $Fe(OR)_3$, $Co(OR)_2$, $Ni(OR)_2$, $Cu(OR)_2$, $Zn(OR)_2$, $Cd(OR)_2$, $Hg(OR)_2$, $B(OR)_3$, $Al(OR)_3$, $In(OR)_3$, $Si(OR)_4$, $Ge(OR)_4$ and $Sn(OR)_4$, $Pb(OR)_2$, $Bi(OR)_3$, where R=methyl, ethyl, propyl, iso-propyl, butyl, sec-butyl, tert-butyl, acetyl can be used. Preferably, silica based precursors are used.

The most suitable metal alkoxides are those having about 1 to 6 carbon atoms, preferably from 1 to 4 carbon atoms in each side chain. Specific examples of such compounds include tetra-ethoxysilane (TEOS), tetramethoxysilane (TMOS), tetra-n-propoxysilane, aluminum isopropoxide, aluminum sec-butoxide, cerium isopropoxide, hafnium tert-butoxide, magnesium aluminum isopropoxide, yttrium isopropoxide, titanium isopropoxide, zirconium isopropoxide, and the like. In the case of silica precursors, these materials can be partially hydrolyzed and stabilized at low pH as polymers of polysilicic acid esters such as polydiethoxysiloxane. These materials are commercially available in alcohol solution from vendors such as Degussa Corporation, Silbond Corporation etc. Pre-polymerized silica precursors are especially preferred for the processing of gel materials described in this invention. The most suitable hydrolysable polymer is alkoxysilyl-containing polymer. Specific examples of such compounds include trimethoxysilyl-containing polymethylmethacrylate, triethoxysilyl-containing polymethylmethacrylate, and trimethoxysilyl containing polybutylmethacrylate, triethoxysilyl containing polybutylmethacrylate, and the like. These trialkoxylsilyl containing polymethacrylate polymers are synthesized from methacrylate monomer, together with trimethoxysilylpropylmethacrylate. The methacrylate monomer includes and is not limit to methylmethacrylate (referred as MMA there after), ethylmethacrylate (referred as EMA there after), butylmethacrylate (referred as BMA there after), hydroxyethylmethacrylate (referred as HEMA there after) and hexafluorobutyl methacrylate (referred as HFBMA there after). Trimethoxysilylpropylmethacrylate has both a polymerizable methacrylate component and reactive trimethoxysily function. The hydrolysis and condensation of this compound will link it into the silica network, while the polymerization of this compound will link it into the polymethacrylate (PMA) phase. In principle this cross-linker will act as a hook between the silica network and the polymethacrylate linear polymer. Inducing gelation of metal oxide or metal oxide/polymer sols in alcohol solutions is referred to as the alcogel process in the present description. Preparation of silica-polymethacrylate hybrid aerogels is for example described in US 2005-0192366 A1.

According to a further embodiment, the present invention thus is directed to the process for preparing an inorganic aerogel as disclosed above, wherein the inorganic aerogel is a silica based aerogel.

Major variables in the inorganic aerogel formation process include the type of alkoxide, the solution pH, and the alkoxide/alcohol/water ratio as well as temperature, nature of the solvent and concentration of the alkoxide. Change of the variables can permit control of the growth and aggregation of the matrix species throughout the transition from the sol state to the gel state. It is useful to be able to control this transition precisely. While properties of the resulting aerogels are strongly affected by the pH of the precursor solution and the molar ratio of the reactants, any pH and any molar ratio that permits the formation of gels may be used in embodiments of the present invention.

The reaction temperature might be in the range of from 0 to 100° C., preferably 5 to 75° C., in particular 10 to 50° C. The sol concentration, i.e. the concentration of reagents in the solvent might be in the range of from 10 to 65 wt %, preferably 15 to 60 wt %, in particular 20 to 55 wt %.

In principle, any solvent can be used as long as it is miscible with carbon dioxide or has a sufficient boiling point which allows for removal of the solvent from the resulting gel. Generally, the solvent will be a low molecular organic compound, i.e. an alcohol having 1 to 6 carbon atoms, preferably 2 to 4, although other liquids known in the art can be used. Possible solvents are, for example, ketones, aldehydes, alkyl alkanoates, amides such as formamide, N-methylpyrrollidone, N-ethylpyrrollidone, sulfoxides such as dimethyl sulfoxide, aliphatic and cycloaliphatic halogenated hydrocarbons, halogenated aromatic compounds and fluorine-containing ethers. Mixtures of two or more of the abovementioned compounds are likewise possible. Examples of other useful liquids include but are not limited to: ethyl acetate, ethyl acetoacetate, acetone, dichloromethane, iso-propanol, methylethylketone, tetrahydrofurane, propylenecarbonate, and the like.

Further possibilities of solvents are acetals, in particular diethoxymethane, dimethoxymethane and 1,3-dioxolane.

Dialkyl ethers and cyclic ethers are likewise suitable as solvent. Preferred dialkyl ethers are, in particular, those having from 2 to 6 carbon atoms, in particular methyl ethyl ether, diethyl ether, methyl propyl ether, methyl isopropyl ether, propyl ethyl ether, ethyl isopropyl ether, dipropyl ether, propyl isopropyl ether, diisopropyl ether, methyl butyl ether, methyl isobutyl ether, methyl t-butyl ether, ethyl n-butyl ether, ethyl isobutyl ether and ethyl t-butyl ether. Preferred cyclic ethers are, in particular, tetrahydrofuran, dioxane and tetrahydropyran.

Aldehydes and/or ketones are particularly preferred as solvent. Aldehydes or ketones suitable as solvent are, in particular, those corresponding to the general formula $R^2$—(CO)—$R^1$, where $R^1$ and $R^2$ are each hydrogen or an alkyl group having 1, 2, 3, 4, 5, 6 or 7 carbon atoms. Suitable aldehydes or ketones are, in particular, acetaldehyde, propionaldehyde, n-butyraldehyde, isobutyraldehyde, 2-ethylbutyraldehyde, valeraldehyde, isopentaldehyde, 2-methylpentaldehyde, 2-ethylhexaldehyde, acrolein, methacrolein, crotonaldehyde, furfural, acrolein dimer, methacrolein dimer, 1,2,3,6-tetrahydrobenzaldehyde, 6-methyl-3-cyclohexenaldehyde, cyanoacetaldehyde, ethyl glyoxylate, benzaldehyde, acetone, diethyl ketone, methyl ethyl ketone, methyl isobutyl ketone, methyl n-butyl ketone, methyl pentylketone, dipropyl ketone, ethyl isopropyl ketone, ethyl butyl ketone, diisobutylketone, 5-methyl-2-acetyl furan, 2-acetylfuran, 2-methoxy-4-methylpentan-2-one, 5-methylheptan-3-one, 2-heptanone, octanone, cyclohexanone, cyclopentanone, and acetophenone. The abovementioned aldehydes and ketones can also be used in the form of mixtures. Ketones and aldehydes having alkyl groups having up to 3 carbon atoms per substituent are preferred as solvent.

Further preferred solvents are alkyl alkanoates, in particular methyl formate, methyl acetate, ethyl formate, isopropyl acetate, butyl acetate, ethyl acetate, glycerine triacetate and ethyl acetoacetate. Preferred halogenated solvents are described in WO 00/24799, page 4, line 12 to page 5, line 4.

Further suitable solvents are organic carbonates such as for example dimethyl carbonate, di-ethyl carbonate, ethylene carbonate, propylene carbonate or butylene carbonate.

In many cases, particularly suitable solvents are obtained by using two or more completely miscible compounds selected from the abovementioned solvents.

After identification of the type of gel material to be prepared using the methods of this invention, a suitable metal alkoxide-alcohol solution, transition metal alkoxide-alcohol solution or semimetal alkoxide-alcohol solution is prepared. For producing silica gel beads useful in the manufacture of silica aerogel materials, preferred ingredients are tetraethoxysilane (TEOS), water, and ethanol (EtOH). The following catalysts can be used to change the pH of the sol in order to induce gelation. While any inorganic as well as organic acid may be used to lower the pH of the sol, $H_3PO_4$, $HNO_3$, HCl, $H_2SO_4$, HF, oxalic acid, benzoic acid, salicylic acid, acrylic acid, icosanoic acid, octadecanoic acid, hexadecanoic acid, tetradecanoic acid, dodecanoic acid, decanoic acid, nonanoic acid, octanoic acid, heptanoic acid, hexanoic acid, pentanoic acid, butanoic acid, propanoic acid, ethanoic acid, methanoic acid, chloroacetic acid, dichloroacetic acid, trichloroacetic acid, trifluoroacetic acid as well as dicarboxylic acids such as molonic acid or adipic acid and tricarboxylic acids such as citric acid and amino acids such as glycine, alanine, valine, leucine, isoleucine, serine, casteine, threonine, methionine, proline, phenylalanine, tyrosine, tryptophane, asparagine, glutamine are preferred. To generate a higher pH, a base like NaOH, KOH, $NH_3$ or $NH_4OH$ can be used.

According to a further embodiment, the present invention thus is directed to the process for preparing an inorganic aerogel as disclosed above, wherein composition (I) comprises at least one alkoxysilane.

In many embodiments, the precursor(s) will be partially or fully hydrolyzed. Non-limiting examples of partial hydrolysis include at least about 1%, at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. Hydrolyzed precursor(s) may be advantageously used because they readily undergo the condensation reaction and thus are responsive to the use of one or more catalyst(s). In other embodiments, the precursor(s) are maintained in an unhydrolyzed form but are hydrolyzed, or subject to hydrolysis (e.g. contact with a hydrolytic agent or exposure to hydrolytic conditions as non-limiting examples), before they are used in the methods of the invention.

Optionally, a catalyst can be used. The catalysts which may be used according to the present invention, may be in solid or liquid form. Non-limiting examples of catalysts include primary, secondary, tertiary amines, amidines and amino acids such as ethylendiamin, diethylentriamin, propylendiamin, 2,3dimethyl-3,4,5,6-tetrahydropyrimidin, triethylamin, tributylamin, dimethyl-benzylamin, N-methyl-, N-ethyl-, N-cyclohexylmorpholin, N,N,N',N'-tetramethylethylendiamin, N,N,N',N'-tetramethyl-butandiamin, N,N,N', N'-tetramethyl-hexandiamin, pentamethyl-diethylentriamin, tetramethyl-diaminoethylether, bis-(dimethylaminopropyl)-urea, dimethylpiperazin, 1,2-dimethylimidazol, 1-aza-bicyclo-(3,3,0)-octan and 1,4-Diaza-bicyclo-(2,2,2)-octan, N,N-dimethylaminopropylamin, bis-(dimethylaminopropyl)-amin, N,N-dimethylaminopropyl urea, N-(2-aminopropyl)-imidazol, histidine, lysine, arginine, aspartate, glutamate as well as ammonia, ammonium hydroxide, potassium hydroxide, or sodium hydroxide.

Properties, especially the morphology, of the resulting aerogels are strongly affected by the pH of the precursor solution. Solution pH affects the processing of aerogels, primarily by controlling the rate of the hydrolysis and condensation reactions. For low temperature aerogels under acidic conditions, hydrolysis of the low temperature aerogel precursors is generally rapid and a burst of metal hydroxide containing monomers is produced which monomers slowly condense by cluster-cluster growth to form a cross-linked gel during the drying. Under basic conditions, the condensation reaction is faster than the hydrolysis reaction and can quickly consume newly generated monomers unless controlled. In this case, the gelation proceeds through monomer-duster growth mechanism. Therefore, in general, especially for low temperature silica aerogels and when flexibility is an important issue, the composite insulations are prepared under neutral to slightly basic conditions, i.e. pH of about 7 to 9, and when flexibility is less desired, more acidic conditions, e.g. pH of about 1 to 5 may be employed.

Furthermore, suitable additives may be used according to the present invention.

For optimal thermal performance, aerogels can be opacified to reduce the radiative component of heat transfer. At any point prior to gel formation, opacifying compounds may be dispersed into the mixture comprising gel precursor. Examples of opacifying compounds include and are not limited to: $B_4C$, Diatomite, Manganese ferrite, MnO, NiO, SnO, $Ag_2O$, $Bi_2O_3$, TiC, WC, carbon black, graphite, titanium oxide, iron, titanium oxide, zirconium silicate, sirconium oxide, iron (I) oxide, iron (III) oxide, manganese dioxide, iron titanium oxide (Ilmenite), chromium oxide, silicon carbide or mixture thereof. Preferably these opacifying components reveal a maximum in the infrared-spectrum in a wave length range from 1.5 to 10 μm. The particle size of these components is preferably between 0.5 to 15 μm. The amount applied in the mixture is preferably between 5 to 20 wt %.

According to a further embodiment, the present invention thus is directed to the process for preparing an inorganic aerogel as disclosed above, wherein the composition (i) comprises further additives.

Factors influencing $t_G$ are for example the ratio of precursor to hydrophobizing agent, water, catalyst (acid/base), reaction temperature, sol concentration, the pH as well as the nature of the solvent used.

The preferred molar ratio of the precursor and hydrophobizing agent to water in the system is 1 to 10, more preferably 1 to 8; and in particular 1 to 6. The preferred molar ratio of acid to base catalyst is 1 to 800, more preferably 1 to 700, and in particular 1 to 600.

Composition (I) is sprayed into supercritical carbon dioxide at a spraying time is to obtain gel particles according to step (ii). In principle, methods for spraying composition (I) are known. According to one embodiment of the present invention, supercritical carbon dioxide is provided, for example in an autoclave, and the reacting composition (I) is sprayed into the autoclave.

According to a preferred embodiment, the autoclave or the volume containing supercritical carbon dioxide is arranged in a way which allows the particles to interact with the carbon dioxide without coming in direct contact with other gel particles. This setup prevents or reduces clogging of particles as well as the spraying inlet.

Typically, the autoclave is operated at a temperature in the range of from 35 to 100° C., preferably from 40 to 85° C., in particular from 45 to 70° C. and at a pressure in the range from 75 to 230 bar, preferably 90 to 180 bar, in particular 105 to 140 bar.

The process of the present invention can also comprise further steps, for example suitable treatment steps. Upon finishing the spraying procedure, the material may for example be cured for a certain time.

The gel particles obtained in step (ii) are dried by supercritical liquid extraction.

For step (iii) of the present invention, generally any method known to the person skilled in the art can be applied. Preferably, carbon dioxide is used for the supercritical liquid extraction according to step (iii).

According to a further embodiment, the present invention is directed to the process as disclosed above, wherein the carbon dioxide is used for the supercritical liquid extraction according to step (iii).

During the extraction, the solvent-$CO_2$ mixture is exchanged successively by pure $CO_2$ which allows for the removal of organic solvent without causing the nano meter-sized pores to collapse, due to the reduced surface tension. In terms of economic efficiency it is preferred to reduce the amount of supercritical liquid extraction steps with $CO_2$. Preferably the supercritical liquid extraction with carbon dioxide is reduced to only one cycle.

At the end of the supercritical extraction the pressure is released in a speed allowing for optimal material properties in combination with a suitable time consumption and the powder is removed from the autoclave.

It has been found that controlling the ratio $t_S:t_G$ allows to obtain an inorganic aerogel with improved particle size and porosity.

Within the preferred ratio of $t_S:t_G$, stable, dry and highly porous aerogel particles are obtained with high surface areas and a high pore volume.

According to the present invention, the ratio $t_S:t_G$ is in the range of from 0.2 to 0.99. Preferably, the ratio is in the range of from 0.4 to 0.95, preferably from 0.45 to 0.90, in particular the ratio is in the range of from 0.50 to 0.85.

It has been found that it is advantageous to control the ratio $t_S:t_G$ to obtain an aerogel with defined surface area and a high pore volume. It has surprisingly been found that outside the range according to the present invention no aerogel particles could be obtained or only particles with insufficient properties.

According to a further embodiment, the present invention thus is directed to the process for preparing an inorganic aerogel as disclosed above, wherein the ratio $t_S:t_G$ is in the range of from 0.4 to 0.95

According to the present invention, the reacting sol is injected into the autoclave with a flow rate in the range from 10 to 999 ml/min. Preferably, with a flow rate in the range from 15 to 950 ml/min, preferably from 20 to 900 ml/min, in particular the flow rate is in the range of from 25 to 850 ml/min.

According to the present invention it is possible to use a hydrophobizing agent in the preparation process to modify the properties of the aerogel. Suitable methods are known to the person skilled in the art. Generally, a hydrophobizing agent is added to the reaction mixture. Suitable hydrophobizing agents are for example low molecular organosilanes or high molecular silicon polyols. Suitable concentrations of the hydrophobizing agent are for example in the range from 0.5 to 55 wt %, preferably 0.7 to 50 wt %, more preferably in the range from 1 to 45 wt %.

As organosilanes, preferably compounds are used selected from the group consisting of formulas $R_n$—Si—$X_{4-n}$, $R_3Si$—Y—$SiR_3$, $R_nSi_nO_n$ and/or $(CH_3)_3$—Si—(O—$Si(CH_3)_2)_n$—OH, and HO—$Si(CH_3)_2$—(O—$Si(CH_3)_2)_n$—OH, where n may be =1, 2, 3, 4, 5, 6, 7 or 8; R represents $CH_3$, and/or —H, —$C_2H_5$, X is Cl or Br, —$OCH_3$, —$OC_2H_5$, —$OC_3H_7$, and Y is NH or O.

Suitable compounds are trimethylchlorosilane, dimethyldichlorosilane, monomethyltrichlorosilane, trimethylethoxysilane, dimethyldiethoxysilane, methyltriethoxysilane, hexamethyldisilazane, hexamethyldisiloxane, octamethyltetracyclosiloxane, or hexamethyltricyclosiloxane. Trimethylchlorosilane, dimethyldichlorosilane, hexamethyldisilazane, hexamethyldisiloxane, octamethyltetracyclosiloxane are preferably used.

Suitable high molecular silicon polyols might have an average molecular weight in the range from 500 to 2500, for example in the range from 600 to 2000. Preferably, high molecular silicon polyols with alkoxy side chains are used. Preferably compounds are used selected from the group consisting of formulas $(CH_3)_3$—$Si(O$—$Si(CH_3)_2)_n$-$(Q)_m$-Y and Y-$(Q)_m$-$Si(CH_3)_2$—(O—$Si(CH_3)_2)_n$-$(Q)_m$-Y, where n may be =1, 2, 3, 4, 5, 6, 7 or 8; m may be in the range from 5 to 20, preferably from 5 to 10, each Q independently represents a group —$(CH_2)_2$—O— or —$CH_2$—$CH(CH_3)$—O—, and Y is $NH_2$ or OH. Suitable compounds are for example difunctional polyols having hydroxyl end groups of the general formulas $(CH_3)_3$—$Si(O$—$Si(CH_3)_2)_n$-$(Q)_m$-OH and HO-$(Q)_m$-$Si(CH_3)_2$—(O—$Si(CH_3)_2)_n$-$(Q)_m$-OH, where n may be =1, 2, 3, 4, 5, 6, 7 or 8; m may be in the range from 5 to 20, preferably from 5 to 10, and each Q independently represents a group —$(CH_2)_2$—O— or —$CH_2$—$CH(CH_3)$—O—. Particularly preferred are dialkylsiloxanes, such as dimethylsiloxane, with alkoxy side chains.

Alternatively, the aerogel can be prepared without using a hydrophobizing agent and the resulting material can be hydrophobized in the gas phase. Suitable methods are known to the person skilled in the art. Generally, the aerogel is pressurized at low pressure with one or more organosilanes in form of a vapor in a suitable gas chamber. Preferably, the pressure in the chamber before introducing the organosilane is less than atmospheric pressure, for example in the range of 0.1 mbar to atmospheric pressure.

It is for example possible to use the vacuum method. According to this embodiment, the organosilane is optimally distributed in the pores of the aerogel. The method is characterized, inter alia, in that the organosilane is present in vapor form in the chamber under the reaction conditions. The organosilane itself can be introduced in liquid or vapor form into the chamber.

As organosilanes, preferably compounds are used selected from the group consisting of formulas $R_n$—Si—$X_{4-n}$, $R_3Si$—Y—$SiR_3$, $R_nSi_nO_n$ and/or $(CH_3)_3$—$Si(O$—Si$(CH_3)_2)_n$—OH, and HO—$Si(CH_3)_2$—(O—$Si(CH_3)_2)_n$—OH, where n may be =1, 2, 3, 4, 5, 6, 7 or 8; R represents $CH_3$, and/or —H, —$C_2H_5$, X is Cl or Br, —$OCH_3$, —$OC_2H_5$, —$OC_3H_7$, and Y is NH or O.

Suitable compounds are trimethylchlorosilane, dimethyldichlorosilane, monomethyltrichlorosilane, trimethylethoxisilane, dimethyldiethoxisilane, methyltriethoxysilane, hexamethyldisilazane, hexamethyldisiloxane, octamethyltetracyclosiloxane, or hexamethyltricyclosiloxane. Trimethylchlorosilane, dimethyldichlorosilane, hexamethyldisilazane, hexamethyldisiloxane, octamethyltetracyclosiloxane are preferably used.

The reaction conditions such as the amount of organosilane used and the contact time can vary in wide ranges. For example the temperature during the treatment is generally in the range from 20 to 300° C. Suitable conditions are for example disclosed in WO 2012/041823 A1. The organosilane may be used as such or in combination with a second compound. Suitable additional compounds which may be applied simultaneously or subsequently are for example water, alcohols and/or hydrogen halides.

The product obtained in the process of the present invention is a micrometer-sized powder of porous inorganic aerogel with a porosity of at least 70 vol. %, in particular a silica aerogel.

Generally, the size of the particles may vary, the particle size is in the range from 0.5 µm to 2 mm, preferably in the range from 0.75 µm to 1.5 mm, in particular in the range from 1 µm to 1 mm.

In further embodiments, the aerogel comprises average pore diameters from about 2 nm to about 100 nm. In additional embodiments, the average pore diameters of dried gel materials may be about 4 nm, about 6 nm, about 8 nm, about 10 nm, about 12 nm, about 14 nm, about 16 nm, about 18 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, or about 95 nm.

In the context of the present invention, the surface area, the pore sizes as well as the pore volumes were measured by BET in accordance with ISO 9277:2010 unless otherwise noted. This International Standard specifies the determination of the overall specific external and internal surface area of disperse (e.g. nano-powders) or porous solids by measuring the amount of physically adsorbed gas according to the Brunauer, Emmett and Teller (BET) method. It takes account of the International Union for Pure and Applied Chemistry (IUPAC) recommendations of 1984 and 1994.

According to a further aspect, the present invention is also directed to the inorganic aerogel obtained or obtainable by a process as disclosed above.

According to a further embodiment, the present invention is directed to the inorganic aerogel as disclosed above, wherein the inorganic aerogel is a silica based aerogel.

The inorganic aerogels obtained or obtainable by the process of the present invention are suitable for different applications.

The present invention is also directed to the use of porous materials as disclosed above or a porous material obtained or obtainable according to a process as disclosed above as thermal insulation material or as core material for vacuum insulation panels.

The invention also relates to construction materials and vacuum insulation panels comprising the powder form nanoporous materials and the use of powder form nanoporous materials for thermal insulation. Preferably, the materials obtained according to the invention are used for thermal insulation especially in buildings, or for cold insulation, particularly in mobile, transportation applications or in stationary applications, for example in cooling devices or for mobile applications.

For mechanical reinforcement fibers can be used as additives. These fibers may be of inorganic or organic origin. Examples of inorganic fibers are glass wool, rock wool, basalt fibers, slag wool, ceramic fibers made from molten aluminum and/or silica and other inorganic metal oxides, and also pure silica fibers. Organic fibers are, for example, cellulose fibers, textile fibers or plastic fibers. Diameters are preferably in the range of 1 to 12 microns, and 6 to 9 microns in particular. The length might preferably be in the range of 1 to 25 mm, 3 to 10 mm in particular.

For technical and economic reasons, a mixture of inorganic fillers may be added. In the context of the present invention, synthetic modifications of silica, like precipitated silicas, arc silicas, $SiO_2$-containing fly ash, resulting from oxidation of volatile silicon monoxide, in the electrochemical production of silicon or ferrosilicon might be used. As silicas which are produced by leaching of silicates such as calcium silicate, magnesium silicate, and mixed silicates, like olivine (magnesium iron silicate) prepared using acids might be used. Also suitable for use are naturally occurring $SiO_2$-containing compounds such as diatomaceous earth. Also thermally bloated perlite and vermiculite minerals can be used. Depending on requirements, preferably finely divided metal oxides such as, preferably, alumina, titanium dioxide, iron oxide can be added.

After completion of the mixing process the tap density of the mixture, depending on the type and amount of the components, preferably is between 40 to 180 kg/m$^3$, more preferably 40 to 90 kg/m$^3$, respectively. The flowability of the resulting porous mixture is very good, so that they can easily and homogeneously be pressed into plates or can be filled into the cavities of hollow blocks. When pressing to sheets it is possible to influence the properties of the plate like plate thicknesses, the weight, density, and consequently the thermal conductivity of the insulating material. The lower the density of the plates, the better are the insulation properties.

The materials used in thermal insulation materials are preferably used in the following fields of application: as insulation in hollow blocks, as core insulation for multi-shell building blocks, as core insulation for vacuum insulation panels (VIP), as the core insulation for exterior insulation systems, as insulation for cavity wall works, especially in the context of loose-fill insulation.

A further object of the present invention are molded articles, building blocks or modules, building systems and building composites which contain or consist of the powdery material according to the present invention. Another object of the present invention are vacuum insulation panels which contain powdery nanoporous materials according to the present invention. Furthermore, the thermal insulation material and the powdery nanoporous materials are in particular suitable for the insulation of extruded hollow profiles, particularly as the core material for the insulation in window frames.

The thermal insulation material is for example an insulation material which is used for insulation in the interior or the exterior of a building or as wall cavity insulation. The porous material according to the present invention can advantageously be used in thermal insulation systems such as for example composite materials. The powdery materials according to the present invention are for example suitable as core material for vacuum insulation panels which are used for insulation in transportation applications. They might be used as interior lining with advantageous insulating properties, for example as interior lining for vehicles. It has been found advantageous to use powdery materials since the respective parts for transportation applications, for example for vehicle construction might have complex shapes.

The powdery materials according to the present invention can for example be used as insulating materials as core material in hollow components, for example in hollow blocks.

Hollow components in the context of the present invention are components which have one or more cavities. They might be prepared from inorganic ceramic materials, such as burnt clay (brick), concrete, glass, gypsum, and natural products such as natural stone, such as limestone exist. Preferably, hollow blocks made of brick, concrete and lightweight concrete are used. Further embodiments are for example wall blocks, floor tiles, ceiling panels and stem elements.

It is known that the cavities of these elements may be filled with insulation materials such as Perlite foam or polystyrene foam. These components are referred to as hollow blocks with integrated thermal insulation.

The use of hollow blocks with integrated thermal insulation to ensure a particularly high thermal insulation also the heat storage should be favored. The inventive use of the porous heat insulating materials described in hollow blocks, the thermal properties of these stones are significantly improved and sustained at a high level. Furthermore, heat insulation plates can be size-swaged and integrated into the chambers of the hollow blocks. Alternatively, plates can be dimensionally accurate cut out from large sheets previously prepared and incorporated into the modules.

To ensure a good balance of the insulation properties obtained and economic factors, combinations of the porous materials according to the invention and conventional insulating materials might be used. Furthermore, it is possible according to the invention to fill the cavities of the hollow components only partly.

According to a further aspect, the present invention is also directed to the use of an inorganic aerogel as disclosed above or an inorganic aerogel obtained or obtainable by a process as disclosed above as catalyst support, for the preparation of sensors as additive for food applications or for medical, pharmaceutical and cosmetic applications Within cosmetic applications the inorganic aerogels obtained or obtainable by the process of the present invention can be used for example as deodorant active agent which is one method for the treatment of human body odors. These can be provided in all forms which can be envisaged for a deodorant composition. It can be a lotion, dispersion as a spray or aerosol; a cream, in particular dispensed as a tube or as a grating; a fluid gel, dispensed as a roll-an or as a grating; in the form of a stick; in the form of a loose or compact powder, and comprising, in this respect, the ingredients generally used in products of this type which are well known to a person skilled in the art, with the proviso that they do not interfere with the aerogels in accordance with the invention.

The concentrations of hydrophobic aerogel to be used in the deodorant compositions depend in particular on the formulation form of the composition. Thus, the concentration of hydrophobic aerogel in a composition can vary from 0.1 to 80% by weight, with respect to the total weight of the composition, for example from 0.1% by weight, in the case of a formulation in the aerosol form, to 80% by weight, in the case of a loose powder. Non-silica based inorganic aerogels are being formed via an analogoues mechanism from the corresponding oxides or alkoxides as silica based aerogels. The major difference here is the much higher reactivity towards water as compared to the corresponding alkoxisilanes. This on the one hand originates from the lower electronegativity as well as higher lewis-acidity of the central metal atoms and on the other hand from the possibility to increase the coordination number. For the present invention this means, that silica based reagents are advantageous in terms of handling within the experimental set up.

According to a further embodiment, the present invention is directed to the use of an inorganic aerogel as disclosed above, wherein the inorganic aerogel is a silica based aerogel.

The present invention includes the following embodiments, wherein these include the specific combinations of embodiments as indicated by the respective interdependencies defined therein.

1. Process for preparing an inorganic aerogel, the process comprising the steps
    (i) providing a composition (I) suitable to form an inorganic gel with a gelation time $t_G$,
    (ii) spraying the composition (I) into supercritical carbon dioxide at a spraying time $t_S$ to obtain gel particles,
    (iii) drying the gel particles obtained in step (ii) by supercritical liquid extraction,
    wherein the ratio $t_S:t_G$ is in the range of from 0.2 to 0.99.
2. The process according to embodiment 1, wherein the inorganic aerogel is a silica based aerogel.
3. The process according to embodiment 1 or 2, wherein composition (I) comprises at least one alkoxysilane.
4. The process according to any one of embodiments 1 to 3, wherein the ratio $t_S:t_G$ is in the range of from 0.4 to 0.95
5. The process according to any one of embodiments 1 to 4, wherein the composition (i) comprises further additives.
6. The process according to any one of embodiments 1 to 5, wherein the carbon dioxide is used for the supercritical liquid extraction according to step (iii).
7. An inorganic aerogel obtained or obtainable by a process according to any one of embodiments 1 to 6.
8. The aerogel according to embodiment 7, wherein the inorganic aerogel is a silica based aerogel.
9. Use of an inorganic aerogel according to embodiment 7 or 8 or an inorganic aerogel obtained or obtainable by a process according to any of claims 1 to 6 for medical and pharmaceutical applications, as additive for food, as catalyst support, for the preparation of sensors, for thermal insulation, or as core material for VIPs.
10. The use of embodiment 9, wherein the inorganic aerogel is a silica based aerogel.

Examples will be used below to illustrate the invention.

EXAMPLES

Process for Preparing Silica Aerogel Powder by Spraying into Supercritical $CO_2$ 1. Acidic Hydrolysis A PP-beaker was charged with 170.4 mg hydrochloric acid, 1.36 g water, 7.68 g ethanol, tetraethoxysilane (TEOS) as well as dimethyl diethoxysilane (DMDEOS) in the amounts given in Table 1 and the solution was stirred for 30 min at room temperature. Thereafter the solution was diluted with 100 ml of acetone and homogenized by stirring.

2. Basic Condensation

In parallel a second PP-beaker was subsequently charged with 816 mg water, 3.92 g $NH_3$ which was added in water and 7.68 g ethanol and the solution was homogenized by stirring. At the end of the above mentioned 30 min, the afore mentioned acidic solution was poured into the basic solution and the mixture was stirred for 30 sec. before the stirrer was removed.

The gelling sol was placed in a syringe pump and was sprayed (with 90 ml/min) at a defined relative spray time $t_S/t_G$ (=absolute spray time is (from mixing acidic and basic solution)/gelation time $t_G$ into an autoclave prefilled with superdritical CO2 (p=120-140 bar, T=50-60° C.). Waiting time, before starting supercritical extraction (=Exchange of auto-clave-atmosphere by fresh $CO_2$) was varied but had no influence on the product quality. After supercritical extraction the autoclave was vented and the product, a white powder, was removed.

As known by the specialist, hydrophobic silica aerogels can be prepared by adding hydrophobizing agents (e.g. alkyl chlorosilanes or alkyl alkoxysilanes) to the sol. This is also transferable to the process described herein.

TABLE 1

| Reagent | Exp. 1-11 Amount [g] | Exp. 12-22 Amount [g] |
|---|---|---|
| TEOS | 34.76 | 33.68 |
| DMDEOS | — | 0.76 |
| EtOH | 7.68 | 7.68 |
| Water | 1.36 | 1.36 |
| HCl | 0.17 | 0.17 |
| NH3 | 3.92 | 3.92 |
| Water | 0.82 | 0.82 |
| EtOH | 7.68 | 7.68 |

The reacting sol was injected into the autoclave with a flow rate of constant 90 ml/min. From the experimental data it becomes obvious, that the relative spray time $t_S/t_G$ has a significant influence on the quality of the prepared silica aerogel powder, whereas the waiting time before supercritical extraction has no influence (Table 2). With increasing relative spray time $t_S/t_G$ the aerogel surface area and the pore volume increase. The same trend is observed when hydrophobic aerogel powders were prepared via the process described herein. If the material is sprayed at a relative spray time of one or greater than one (after the point of gelation of the specific system), no product is obtained.

Pore volumes and BET surface were determined in accordance with ISO 9277:2010.

The invention claimed is:

1. A process for preparing an inorganic aerogel, the process comprising:
    (i) providing a composition (I) suitable to form an inorganic gel with a gelation time $t_G$,
    (ii) spraying the composition (I) into supercritical carbon dioxide at a spraying time $t_S$ to obtain gel particles,
    (iii) drying the gel particles obtained in step (ii) by supercritical liquid extraction,
    wherein the ratio $t_S:t_G$ is in the range of from 0.2 to 0.99, wherein the inorganic aerogel is a silica based aerogel.

2. The process according to claim 1, wherein composition (I) comprises at least one alkoxysilane.

3. The process according to claim 1, wherein the ratio $t_S:t_G$ is in the range of from 0.4 to 0.95.

4. The process according to claim 1, wherein the composition (i) further comprises an additive.

5. The process according to claim 1, wherein the carbon dioxide is used for the supercritical liquid extraction according to step (iii).

6. A process for preparing an inorganic aerogel, the process comprising:
    (i) providing a composition (I) suitable to form an inorganic gel with a gelation time $t_G$, wherein the composition (I) comprises at least one alkoxysilane,
    (ii) spraying the composition (I) into supercritical carbon dioxide at a spraying time $t_S$ to obtain gel particles,
    (iii) drying the gel particles obtained in step (ii) by supercritical liquid extraction,
    wherein the ratio $t_S:t_G$ is in the range of from 0.2 to 0.99.

7. The process according to claim 6, wherein the ratio $t_S:t_G$ is in the range of from 0.4 to 0.95.

TABLE 2

| | | spray conditions | | | | | RESULT | |
|---|---|---|---|---|---|---|---|---|
| | ambient | absolute | relative | | | | | |
| Exp. No. | gelation gel time $t_g$ [min] | spray time $t_s$ [min] | spray time $t_s/t_g$ | autoclave pressure [bar] | waiting time [h] | autoklave temperature [° C.] | surface area [m²/g] | pore volume cc/g |
| 1 | 17 | 2 | 0.12 | 130 | 1 | 53 | 128 | 0.34 |
| 2 | 17 | 2 | 0.12 | 134 | 1 | 55 | 177 | 0.59 |
| 3 | 14 | 2 | 0.14 | 138 | 15 | 56 | 76 | 0.32 |
| 4 | 20 | 8 | 0.40 | 139 | 1 | 55 | 367 | 0.99 |
| 5 | 20 | 8 | 0.40 | 136 | 1 | 55 | 362 | 0.76 |
| 6 | 13 | 8 | 0.62 | 131 | 15 | 55 | 407 | 1.37 |
| 7 | 17 | 14 | 0.82 | 137 | 1 | 55 | 535 | 2.2 |
| 8 | 18 | 13 | 0.72 | 133 | 1 | 55 | 647 | 2.75 |
| 9 | 14 | 11 | 0.79 | 135 | 1 | 53 | 554 | 4.4 |
| 10 | 18 | 15 | 0.83 | 134 | 15 | 55 | 462 | 2.35 |
| 11 | 17 | 20 | 1.18 | 132 | 1 | 54 | — | — |
| 12 | 34 | 2 | 0.06 | 130 | 1 | 53 | 333 | 0.6 |
| 13 | 31 | 2 | 0.06 | 131 | 1 | 56 | 299 | 0.43 |
| 14 | 33 | 2 | 0.06 | 138 | 0.25 | 53 | 205 | 0.36 |
| 15 | 28 | 2 | 0.07 | 136 | 0.25 | 50 | 241 | 0.2 |
| 16 | 39 | 15 | 0.38 | 129 | 0.25 | 55 | 611 | 2.07 |
| 17 | 40 | 15 | 0.38 | 134 | 1 | 54 | 411 | 1.25 |
| 18 | 34 | 15 | 0.44 | 138 | 1 | 55 | 507 | 2.39 |
| 19 | 40 | 30 | 0.75 | 133 | 0.25 | 53 | 653 | 2.3 |
| 20 | 36 | 30 | 0.83 | 134 | 1 | 55 | 698 | 2.34 |
| 21 | 38 | 30 | 0.79 | 139 | 1 | 55 | 647 | 2.77 |
| 22 | 37 | 42 | 1.14 | 135 | 1 | 53 | — | — |

8. The process according to claim 6, wherein the composition (i) further comprises an additive.

9. The process according to claim 6, wherein the carbon dioxide is used for the supercritical liquid extraction according to step (iii).

* * * * *

UNITED STATES PATENT AND TRADEMARK OFFICE
CERTIFICATE OF CORRECTION

PATENT NO. : 10,544,049 B2
APPLICATION NO. : 15/528308
DATED : January 28, 2020
INVENTOR(S) : Wibke Loelsberg et al.

It is certified that error appears in the above-identified patent and that said Letters Patent is hereby corrected as shown below:

In the Specification

Column 2, Line 1, "SEDS" should read --SDS--

Column 4, Line 53, "praesodym" should read --praseodymium--

Column 4, Line 63, "praesodym" should read --praseodymium--

Column 6, Lines 49-50, "cyclocyclohexenaldehyde" should read --cyclohexanaldehyde--

Column 7, Line 25, "molonic" should read --malonic--

Column 7, Line 27, "casteine" should read --cysteine--

Column 7, Line 58, "2,3dimethyl" should read --2,3-dimethyl--

Column 8, Lines 33-34, "sirconium" should read --zirconium--

Column 8, Lines 36-37, "opacifiying" should read --opacifying--

Column 8, Line 56, "is" should read --$t_S$--

Column 9, Line 51, "0.95" should read --0.95.--

Column 13, Line 57, "analogoues" should read --analogous--

Column 14, Line 24, "0.95" should read --0.95.--

Column 14, Line 66, "is" should read --$t_S$--

Signed and Sealed this
Eighteenth Day of August, 2020

Andrei Iancu
*Director of the United States Patent and Trademark Office*

CERTIFICATE OF CORRECTION (continued)
U.S. Pat. No. 10,544,049 B2

Column 14, Line 66, "(from" should read --from--

Column 15, Line 1, "superdritical CO2" should read --supercritical $CO_2$--

Column 15, Line 23, "NH3" should read --$NH_3$--

Columns 15-16, Line 50, "autoklave" should read --autoclave--